United States Patent [19]

Kobayashi et al.

[11] 4,016,193
[45] Apr. 5, 1977

[54] NOVEL SUBSTITUTED PHENYLACETIC ACID DERIVATIVES AND A PROCESS FOR PREPARING THEREOF

[75] Inventors: Toshihiko Kobayashi; Hidetoshi Hiranuma; Susumu Mizogami; Hiroyoshi Nishi; Mamoru Higuchi; Masatoshi Onoya, all of Ami, Japan

[73] Assignee: Mitsubishi Yuka Pharmaceutical Co., Ltd., Tokyo, Japan

[22] Filed: July 3, 1975

[21] Appl. No.: 592,946

[30] Foreign Application Priority Data

July 9, 1974 Japan .............................. 49-78606

[52] U.S. Cl. .................... 260/471 R; 260/465 R; 260/465 K; 260/501.1; 260/521 N; 260/559 R; 424/309; 424/316; 424/317

[51] Int. Cl.² ........................................ C07C 79/46

[58] Field of Search ......... 260/471 R, 521 N, 501.1

[56] References Cited

UNITED STATES PATENTS

| | | |
|---|---|---|
| 3,211,611 | 10/1965 | Clark et al. ................ 260/471 R X |
| 3,503,952 | 3/1970 | Caldwell et al. ........... 260/521 N X |
| 3,547,619 | 12/1970 | Back et al. ................. 260/471 R X |
| 3,786,085 | 1/1974 | Dickel et al. .............. 260/471 R X |

*Primary Examiner*—Richard L. Raymond
*Attorney, Agent, or Firm*—Flynn & Frishauf

[57] ABSTRACT

Novel substituted phenylacetic acid derivatives having the formula:

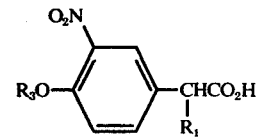

wherein $R_1$ represents a hydrogen atom or lower alkyl radical and $R_3$ represents an alkenyl or alkynyl radical having 3 – 4 carbon atoms with excellent anti-inflammatory and analgesic activities.

9 Claims, No Drawings

NOVEL SUBSTITUTED PHENYLACETIC ACID DERIVATIVES AND A PROCESS FOR PREPARING THEREOF

This invention relates to novel substituted phenylacetic acid derivatives having anti-inflamatory and analgesic activities and a process for preparing them. More particularly, this invention relates to the compounds having the following formula:

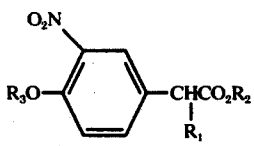

wherein $R_1$ represents a hydrogen atom or lower alkyl radical having 1 - 4 carbon atoms, $R_2$ represents an alkyl or phenyl radical which may be substituted and $R_1$ represents an alkenyl or alkynyl radical, both of which have 3 - 4 carbon atoms
and the compounds having the following formula:

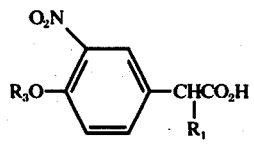

wherein $R_1$ and $R_3$ have the same meaning as defined above
and their pharmaceutical acceptable salt and a process for preparing the above compounds (I) and (II) or their salts.

Heretofore there has been known p-alkenyloxy or p-alkynyloxyphenyl substituted derivatives having anti-inflammatory and analgesic activities (For example, Patent Publication No. Sho48-7421). The inventors of this invention found that after an extensive study the compounds having the above formula (I) and (II) have extremely excellent anti-inflamatory and analgesic activities and completed this invention.

This invention will be described in detail as follows.

According to this invention, the compounds (I) can be prepared by reacting the compounds having the formula (III):

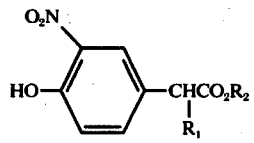

wherein $R_1$ and $R_2$ have the same meanings as above with the compounds having the formula (IV):

$$R_3X \qquad \text{IV}$$

wherein X represents a halogen atom or $-OSO_2\text{-}R_4$ in which $R_4$ represents a lower alkyl or phenyl radical which may be substituted and $R_3$ has the same meaning as above
and the compounds (II) can be prepared by hydrolyzing the compounds (I) in an usual manner and, if necessary the pharmaceutically acceptable salts of the compounds (II) can be prepared in an usual manner.

On the other hand, the compounds having the formula (II) can be also prepared by the following processes: A process which comprises hydrolyzing the compounds having the formula (V):

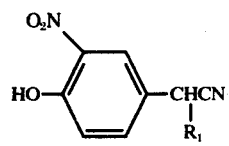

wherein $R_1$ has the same meaning as above to the amido compounds having the formula (VI):

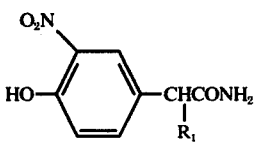

wherein $R_1$ has the same meaning as above, reacting the above compounds (VI) with the compounds having the formula (IV):

$$R_3X \qquad \text{IV}$$

wherein $R_3$ and X have the same meanings as above to obtain the compounds having the formula (VII):

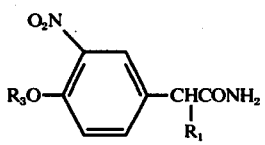

wherein $R_1$ and $R_3$ have the same meanings as above and hydrolyzing the above compounds (VII);
A process which comprises reacting the compounds having the formula (V):

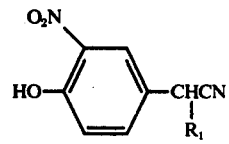

wherein $R_1$ has the same meaning as above with the compounds having the formula (IV):

$$R_3X \qquad \text{IV}$$

wherein $R_3$ and X have the same meanings as above to obtain the compounds having the formula (VIII):

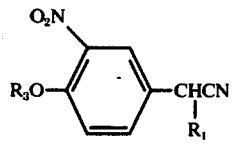

wherein $R_1$ and $R_3$ have the same meanings as above and hydrolyzing the above compounds (VIII).

In the case of hydrolysis of the compounds (VIII), the intermediate compounds having the formula (VII):

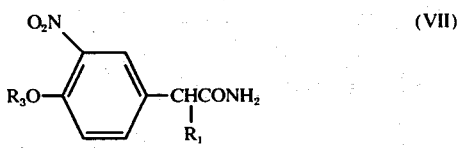

(VII)

may be isolated on the conditions of hydrolysis and in such cases, the compounds (VII) can be hydrolyzed by means of an usual method to give the object compounds (II). The compounds (II) can be transformed, if necessary, into the compounds (I) by esterification or their pharmaceutical acceptable salts.

In the starting compounds having the formula (III), $R_1$ represents a hydrogen atom or a lower alkyl radical having 1 – 4 carbon atoms. As examples of the alkyl radicals, there can be mentioned methyl, ethyl, propyl, isopropyl, butyl and isobutyl radicals. $R_2$ represents an alkyl or a phenyl radical which may be substituted. As examples of the alkyl radicals, there can be mentioned methyl, ethyl, propyl, isopropyl, butyl, isobutyl, pentyl, hexyl, octyl, decyl, dodecyl and the like. As examples of the substituted phenyl radicals, there can be mentioned phenyl radicals which may be substituted with lower alkyl radical such methyl and ethyl, halogen atoms such as chlorine and bromine, lower alkoxyl radicals such as methoxy and ethoxy. But among the alkyl or substituted phenyl radicals, lower alkyl radical having 1 – 4 carbon atoms such as methyl, ethyl, propyl, isopropyl, butyl and isobutyl are preferred.

In the compounds having the formula (IV), $R_3$ represents alkenyl radicals having 3 – 4 carbon atoms such as allyl, crotyl (2-butenyl) and methallyl (2-methylallyl) and alkynyl radical having 3 – 4 carbon atoms such as propargyl and butan-2-ynyl. X represents halogen atoms such as chlorine, bromine and iodide and the $-OSO_2-R_4$ radical represents sulfonic acid residues such as methanesulfonic acid, benzenesulfonic and p-toluenesulfonic acid residue. As examples of the compounds $R_3X$ (IV), there can be mentioned allyl chloride, allyl bromide, allyl iodide, propargyl chloride, propargyl bromide, propargyl iodide, crotyl chloride, crotyl bromide, methallyl chloride, methallyl bromide, allyl methanesulfonate, allyl benzene-sulfonate, allyl p-toluenesulfonate, propargyl methanesulfonate, propargyl benzenesulfonate and propargyl p-toluenesulfonate.

The reaction of the compounds (III) with the compounds (IV) can be carried out in the presence or absence of a solvent. As the solvents used for this reaction, any solvent which does not react with halogenated compound (IV) can be used without limiting. But as solvents, there can be generally used ketones such as acetone, methyl ethyl ketone, diethyl ketone, and methyl propyl ketone, aromatic compounds such as benzene, and toluene, monoalicyclic compounds such as cyclohexane and cyclopentane and alcohols such as methanol, ethyl alcohol, propyl alcohol and butyl alcohol.

To accelerate the reaction rate of this reaction, the use of acid-binding agents is preferred. As acid-binding agents used for this reaction, there can be mentioned carbonates or hydrogen carbonates of alkali or alkaline earth metals such as sodium carbonate, potassium carbonate, lithium carbonate, sodium hydrogen carbonate, potassium hydrogen carbonate, lithium hydrogen carbonate, calcium carbonate, barium carbonate, magnesium carbonate, and calcium hydrogen carbonate, hydroxides of alkali or alkaline earth metals such as sodium hydroxide, potassium hydroxide, lithium hydroxide, magnesium hydroxide and calcium hydroxide, metal amides or hydrides such as sodium amide and sodium hydride and organic bases such as aniline, methylaniline, pyridine, picoline, pyrrolidine, piperidine and methylpiperidine.

In the case of using a large amount of the above organic bases, they play a roll of solvents and the use of other solvents may not be always necessary.

The reaction of the compounds (III) with the compound (IV) according to this invention can be preferred to be generally carried out by refluxing them in the above solvent in the presence of the above acid-binding agent. The reaction time varies with the activity of the compounds (IV) used and the kind of solvents but is usually from 10 minutes to 10 hours. After completion of the reaction, isolation of the object compounds (I) can be carried out in an usual manner. According to the kinds of solvents and acid-binding agents used, after filtration of the acid-binding agents, the object compounds (I) can be isolated by distilling out the solvent from the reaction mixture and extracting the residue with solvents such as ethyl acetate.

The hydrolysis of the compounds (V) to the compounds (VI) can be carried out by means of an usual hydrolysis method of $-CN$ radical to $-CONH_2$. The following methods can be usually applied: (a) a method of using hydrogen peroxide in a solvent in the presence of an alkaline base; (b) a method of using polyphosphoric acid; (c) a method of hydrolysis with inorganic acid or alkali; (d) a method of using nitrite salt or nitrite ester. The above method (a) can be usually carried out by using 3 – 30% hydrogen peroxide in a solvent such as acetone, methanol, ethanol, methyl ethyl ketone, ethers or tetrahydrofuran in the presence of an alkaline base such as sodium hydroxide, potassium hydroxide, sodium carbonate, potassium carbonate, sodium hydrogen carbonate or potassium hydrogen carbonate. The reaction is carried out at 0° – 80°, preferably 20° – 60° C for 30 minutes – 24 hours, preferably 1 – 12 hours. An amount of hydrogen peroxide and alkaline base used for this reaction is 0.8 – 10 moles, preferably 1 – 5 moles per one mole of the nitrile compounds (V). After completion of the reaction, the reaction mixture is neutralized to give the compound (VI). The above reaction (b) can be carried out by using 0.8 – 100 moles, preferably 3 – 20 moles of polyphosphoric acid per one mole of the nitrile compounds (V) at 50° – 150° C preferably 90° – 120° C for 30 minutes to 5 hours, preferably 1 – 3 hours. The above method (c) can be carried out by using an inorganic acid such as hydrochloric acid, sulfuric acid, hydrobromic acid, hydroiodic acid or phosphoric acid, or an alkaline base such as sodium hydroxide, potassium hydroxide, sodium carbonate, or potassium carbonate in an aqueous solvent such as water, alcohols such as methanol, ethanol, propanol, n-butanel, t-butanol, acetic acid, dioxan or tetrahydrofuran at 0° – 150° C, preferably 50° – 100° C for 10 minutes – 24 hours, preferably 1–8 hours. An amount of acid or alkaline base is 1 – 20 moles, preferably 1 – 10 moles per one mole of the nitrile compound (V). The above method (d) can be carried out by using nitrite salt or ester in a solvent such as water, alcohols, for example, methanol, ethanol, propanol, n-butanol, t-butanol or dioxan under addition of hydrochloric acid or sulfuric acid. The reaction is carried out at 0° – 150°

C, preferably 30° – 100° C for 0.5 – 12 hours, preferably 1 – 8 hours. An amount of nitrite salt or ester used for this invention is 0.8 – 6 moles, preferably 1 – 3 moles and that of an acid used 0.8 – 10 moles, preferably 1 – 3 moles per one mole of the nitrile compounds (V).

The reaction of the compounds (VI) with the compound (IV) can be carried out in the same conditions as described in the reaction of the compounds (III) with the compounds (IV).

The hydrolysis of the compounds (VII) can be usually carried out by an usual method used for hydrolysis of amide to — carboxylic acid. For example, the methods (c) and (d) described above can be used in the same conditions as described in the reaction of hydrolysis of the nitrile compounds (V).

The reaction of the compound (V) with the compounds (IV) can be also carried out in the same conditions as described in the reaction of the compounds (III) with the compound (IV).

The hydrolysis of the compounds (VIII) to the compounds (II) can be usually carried out by an usual method used for hydrolysis of nitrile to carboxylic acid. That is, the methods (c) and (d) described above can be used in the same conditions.

The object compounds (I) as well as the free acid (II) of (I), as is clearly described thereinafter, have excellent anti-inflamatory and analygesic activities.

The free acid compounds (II) can be obtained by means of an usual hydrolysis of the compound (I). The hydrolysis can be preferred to be carried out in an alcoholic aqueous solution in the presence of caustic alkali. The hydrolysis can be also carried out with mineral acids such as hydrochloric acid and sulfuric acid.

The compounds (I) and (II) according to this invention are novel compounds.

According to this invention, the following compound can be prepared:

3-nitro-4-allyoxyphenylacetic acid,
3-nitro-4-crotyloxyphenylacetic acid,
3-nitro-4-propargyloxyphenylacetic acid,
3-nitro-4-methallyloxyphenylacetic acid,
3-nitro-4-(butan-2-yloxy)phenylacetic acid,
2-(3-nitro-4-allyloxyphenyl)propionic acid,
2-(3-nitro-4-crotyloxyphenyl)propionic acid,
2-(3-nitro-4-methallyloxyphenyl)propionic acid,
2-(3-nitro-4-propargyloxyphenyl)propionic acid,
2-[3-nitro-4-(butan-2-yloxyphenyl)]propionic acid,
2-(3-nitro-4-allyloxyphenyl)butyric acid,
2-(3-nitro-4-crotyloxyphenyl)butyric acid,
2-(3-nitro-4-methallyloxyphenyl)butyric acid,
2-(3-nitro-4propargyloxyphenyl)butyric acid,
2-[3-nitro-4-(butan-2-yloxyphenyl]butyric acid,
2-(3-nitro-4-allyoxyphenyl)valeric acid,
2-(3-nitro-4-crotyloxyphenyl)valeric acid,
2-(3-nitro-4-methallyloxyphenyl)valeric acid,
2-(3-nitro-4-propargyloxyphenyl)valeric acid,
2-[3-nitro-4-(butan-2-yloxyphenyl)]valeric acid,
Methyl 3-nitro-4-allyloxyphenylacetate,
Methyl 3-nitro-4-crotyloxyphenylacetate,
Methyl 3-nitro-4-methallyloxyphenylacetate,
Methyl 3-nitro-4-propargyloxyphenylacetate,
Methyl 3-nitro-4-butan-2-yloxy)phenylacetate,
Methyl 2-(3-nitro-4-allyloxyphenyl)propionate,
Methyl 2-(3-nitro-4-crotyloxyphenyl)propionate,
Methyl 2-(3-nitro-4-methallyloxyphenyl)propionate,
Methyl 2-(3-nitro-4-propargyloxyphenyl)propionate,
Methyl 2-[3-nitro-4-(butan-2-yloxyphenyl)]propionate,
Methyl 2-(3-nitro-4-allyloxyphenyl)butyrate,
Methyl 2-(3-nitro-4-crotyloxyphenyl)butyrate,
Methyl 2-(3-nitro-4-methallyloxyphenyl)butyrate,
Methyl 2-(3-nitro-4-propargyloxyphenyl)butyrate,
Methyl 2-[3-nitro-4-(butan-2-yloxyphenyl)]butyrate,
Methyl 2-(3-nitro-4-allyloxyphenyl)valerate,
Methyl 2-(3-nitro-4-crotyloxyphenyl)valerate,
Methyl 2-(3-nitro-4-methallyloxyphenyl)valerate,
Methyl 2-(3-nitro-4-propargyloxyphenyl)valerate,
Methyl 2-[3-nitro-4-(butan-2-yloxyphenyl)]valerate.

Also, the salts obtained according to this invention are pharmaceutical acceptable salts such as, for example, alkali metal salts, alkaline earth metal salts, ammonium salts, or amine salts such as mono-, di- or trialkanol amines or cyclic amines.

Among the starting compounds (III) used for this invention, the compounds except the compound in which $R_1$ is a hydrogen atom are novel compounds and can be prepared similarly in the same way as in known similar compounds. For example, 2-(3-nitro-4-hydroxyphenyl)propionate ester can be obtain by methylating p-methoxyphenylmalonic acid ethyl-esternitrile with methyl halides in a alcoholic solvent in the presence of a base, by hydrolyzing the resultant with an acid to obtain 2-(p-methoxyphenyl)propionic acid, then nitrating the above compound and de-etherificating and esterifying the resultant compound.

The above reaction scheme is shown as follows:

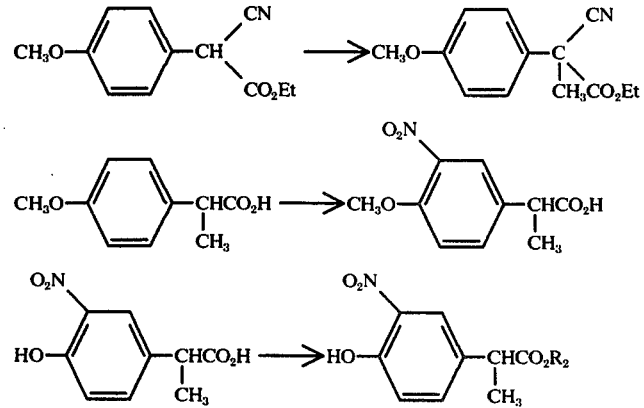

wherein $R^2$ has the same meaning as above

Also, the compounds (III) used for this invention, for example, 2-(3-nitro-4-hydroxyphenyl)propionate can be prepared by demethylating 2-(4-methoxyphenyl)-propionic acid with hydroiodic acid and the like to obtain 2-(4-hydroxyphenyl)- propionic acid, by esterifying the above compound with an usual method to obtain, for example, methyl 2-(4-hydroxyphenyl)propionate and by nitrating the above compounds. Alternately, 2-(3-nitro-4-hydroxyphenyl)propionate can be prepared by nitrating the above 2-(4-hydroxyphenyl)-propionic acid with an usual method and by esterificating the resultant compound. The above reactions can be applied to 4-hydroxyphenylacetate as well. The above reaction scheme is shown as follows:

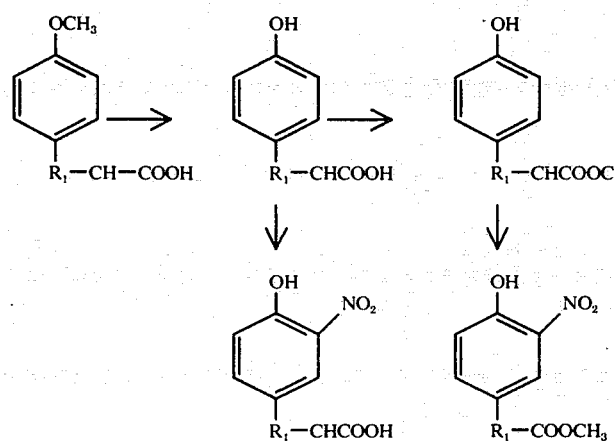

wherein $R_1$ has the same meaning as above

The starting compounds (V) used for this invention can be prepared by the method described in Angyal et al: J. Chem. Soo., 2141 (1950). For example, 3-nitro-4-hydroxybenzyl-chloride is prepared by reaction of nitrophenol and aldehyde with concentrated hydrochloric acid and then converted into nitrile compound by reacting the resultant with nitrilating agents such as sodium cyanide, potassium cyanide and copper cyanide. Next, the pharmacological activities and toxities of the compounds according to this invention will be described:

a Anti-inflamatory activities

The anti-inflamatory activity is shown by inhibiting rate calculated from measurement of carrageenin edema intensity. Five wistar male rats having body weight of 120 – 180g are defined as one group and after fasted for 18 hours, the sample containing a 1% tragacanth solution such as is suspended so as to become 5 ml/kg was administered orally to the said group. Only the same volume of the 1% tragacanth solution was administered to the control group. After one hour, 0.05 ml of a 1% carrageenin (manufactured by Picnin-A, Pasco International Corp.) was injected subcutaneously to the plantar legion of right hind paw of rats. Before injection and after 4 hours of injection of carrageenin, the right hind paw volume was measured by means of paw volume measurement instrument manufactured by Ugo-Basile and an increase % of paw volume was calculated. The inhibiting rate was calculated from an increase ratio of the examined group against the central groups. The results are shown in Table I.

Table 1

| | Name of compounds | dosage(mg/kg) orally | inhibiting rate (%) |
|---|---|---|---|
| | Methyl 3-nitro-4-allyl-oxyphenylacetate | 12.5 | 51.7 |
| | | 25 | 72.1 |
| Compounds | 3-Nitro-4-allyloxy- | 12.5 | 13.9 |
| of this | phenylacetic acid | 25 | 24.3 |
| invention | | 50 | 66.6 |
| | 3-Nitro-4-propargyloxy-phenylacetic acid | 50 | 28.8 |
| | | 100 | 40.3 |
| | Methyl 3-nitro-4-propargyl-oxyphenylacetate | 100 | 44.9 |
| | Methyl 2-(3-nitro-4-alloxyphenyl)propionate | 100 | 50.1 |
| | Ethyl 2-(3-nitro-4-allyloxyphenyl)propionate | 100 | 55.5 |
| | 2-(3-nitro-4-allyl-oxyphenyl)propionic acid | 100 | 40.1 |
| | 3-nitro-4-allyloxy-phenylacetamide | 100 | 37.7 |
| | 3-chloro-4-allyloxy-phenylacetic acid | 25 | 47.0 |
| | | 50 | 51.8 |
| | | 100 | 62.0 |
| Known | Phenylbutazone | 12.5 | 14.1 |
| | | 25 | 49.1 |

Table 1-continued

| Name of compounds | dosage(mg/kg) orally | inhibiting rate (%) |
|---|---|---|
| compounds | 50 | 59.4 |
| Indomethacine | 1 | 39.8 |
| | 3 | 46 |
| | 9 | 60.4 |
| Mepirizole | 25 | 19.5 |
| | 50 | 51.8 |
| | 100 | 52.7 |

(b) The analgesic activity was measured by means of acetic and writhing method. ED50 values of analgesic activity of the compounds according to this invention are shown in Table II. 10dd origin male mice weighing 17 – 25g were used as one group after 18 hours of fasting. After oral administration of the test compounds the frequencies of writhing syndrome caused by intraperitoneal administration of 0.1 ml/10g of a 0.6% acetic acid were measured for 20 minutes. The frequencies of writhing syndrome which are below 50% of those of the control group were defined as analgesic activity (+) and the ED50 values were calculated by means of Litchfield-Wilcoxon method. The ED50 value of methyl 3-nitro-4-allyloxyphenylacetate is defined as 1 and the activity ratios of the test compounds were expressed as ratio of ED50 values. The test compounds were administered as a suspension such as are adjusted to be 0.1 ml/10g in a 1% tragacanth solution. A 1% tragacanth solution was administered to the control group.

Table 2

| | | ED$_{50}$(mg/kg) orally | activity ratio |
|---|---|---|---|
| Compounds of this invention | Methyl 3-nitro-4-allyl-oxyphenyl acetate | 31.0 | 1 |
| | 3-nitro-4-allyloxyphenyl-acetic acid | 96.0 | 0.32 |
| | 3-chloro-4-allyloxy-phenylacetic acid | 56.8 | 0.54 |
| Known compounds | Aminopyrine | 80.0 | 0.38 |
| | Aspirin | 320.0 | 0.09 |
| | Mepirizole | 117.0 | 0.26 |

(c) LD$_{50}$ of the compounds in rats are shown in Table 3.

Table 3

| Name of compounds | LD$_{50}$(mg/kg) orally |
|---|---|
| Compounds of this invention | Methyl 3-nitro-4-allyloxy-phenylacetate | above 3,000 |
| | 3-nitro-4-allyloxyphenyl-acetic acid | 1,475 |
| | | 1,360 |
| | 3-chloro-4-allyoxyphenyl-acetic acid | 1,700 |
| Known compounds | | 1,630 |
| | Mepirizole | 1,022 |
| | | 971 |

From the above experimental results on pharmacological activities and toxities, the compounds according to this invention have a small grade of toxity and excellent antiinflamatory and analgesic activities.

The compounds according to this invention are effectively administered orally, parenterally and non-orally and used in forms of tablets, granules, sugar-coating tablets, capsules, injections or ointments.

The compounds according to this invention are administered in such doses that the desired activity is achieved without secondary effects.

The compounds according to this invention are conveniently administered as a pharmaceutical preparation in dosage unit form containing from 10 mg to 5g, preferably 25 – 500 mg of the active compounds. By the term "dosage unit" is meant a unitary, i.e. a single dose capable of being administered to a patient, and which may be readily handled and packed, remaining as a physically stable unit dose, comprising either the active material as such or in a mixture of it with a pharmaceutical carrier and auxiliary agents. In the form of a dosage unit the compounds may be administered one or more times a day at appropriate intervals. The daily dose usually amounts to from 10mg to 10g preferably 50mg to 3g always depending, however, on the condition of the patients.

In pharmaceutical compositions containing the present compounds organic or inorganic, solid or liquid carriers suitable for oral, enteral or parenterral administration can be used to make up the composition. Crystalline cellulose, gelatine, lactose, starch, magnesium stearate, talc, vegetable and animal fats and oils, gum, polyalkylene glycol or other known carriers for medicaments are all suitable as carriers. In the pharmaceutical compositions, the proportion of therapeutically active material to carrier substances can vary between 0.5 per cent and 100%. The compositions may further contain other therapeutic compounds having anti-inflammatory and analgesic activity, besides the well-known auxiliary agents.

Next, this invention will be illustrated in detail by the following examples. But these examples are meant to limit the scope of this invention.

EXAMPLE 1

Methyl 3-nitro-4-allyloxyphenylacetate

A mixture of 11.5g of methyl 3-nitro-4-hydroxyphenylacetate, 7.9g of allylbromide and 8.9g of potassium carbonate was refluxed in 100ml of acetone for 4 hours. After cooling, the solvent was distilled off under reduced pressure and the residue was dissolved in ethyl acetate and washed with water. After the solution was dried over magnesium sulfate, the solvent was distilled off and the thus obtained crystals were recrystallized from metanol to give the object compound having m.p. 52° – 53° C. Yield, 12.57g (94.1%)

Elementary analysis for $C_{12}H_{13}NO_5$ (%) Calculated: C, 57.37; H, 5.22; N, 5.58 Found : C, 57.19; H, 5.55; N, 5.52 Infrared spectrum (KBr, cm$^{-1}$): 1350, 1530 (NO$_2$); 1730 (CO)

EXAMPLE 2

3-Nitro-4-allyloxyphenylacetic acid

In mixed solution of 5.7g of sodium hydroxide, 30ml of water and 10ml of methanol 11.8g of methyl 3-nitro-4-allyloxyphenylacetate was added and the mixture was heated on a water bath for 30 minutes. After cooling, the solution was filtered and neutralized with 10% hydrochloric acid to give crystals, which were recrystallized from ether-petrolium ether. m.p. 93° – 94° C. Yield, 9.5g (85%)

Elementary analysis for $C_{11}H_{11}NO_5$ Calculated: C, 55.69; H, 4.67; N, 5.91 Found : C, 55.40; H, 4.69; N, 5.68 Infrared spectrum (KBr, cm$^{-1}$): 1340, 1520 (NO$_2$); 1695 (CO); 3000 (OH)

EXAMPLE 3

Methyl 3-nitro-4-propargyloxyphenylacetate

In 30ml of acetone a mixture of 1.06g of methyl 3-nitro-4-hydroxyphenylacetate, 0.6g of propargyl bromide and 0.7g of sodium carbonate was refluxed for 4 hours. After cooling, the solvent was distilled off under reduced pressure and the residue was dissolved in ethyl acetate and washed with water. The solution was dried over magnesium sulfate and concentrated. The thus obtained crystals were recrystallized from methanol to give the object compound having m.p. 66° – 68° in a yield of 0.74g (70%).

Elementary analysis for $C_{12}H_{11}NO_5$ Calculated: C, 57.83; H, 4.45; N, 5.62 Found : C, 57.89; H, 4.74; N, 5.48 Infrared spectrum (KBr, cm$^{-1}$):

| 1350, 1530 | (NO$_2$) |
| 1720 | (CO) |
| 2100 | (C≡C) |
| 3220 | (C≡CH) |

EXAMPLE 4

3-Nitro-4-propargyloxyphenylacetic acid

In a mixed solution of 0.5g of sodium hydroxide, 5 ml of water and 2ml of metanol 0.7g of methyl 3-nitro-4-propargyloxyphenylacetate was added and heated on a water bath for 30 minutes. After cooling, the solution was neutralized with 10% hydrochloric acid and the thus obtained crystals were recrystallized from ether-n-hexane to give the object compound having m.p. 135° – 137° C in a yield of 0.6g (90.6%).

Elementary analysis for $C_{11}H_9NO_5$ (%) Calculated: C, 56.17; H, 3.86; N, 5.96 Found : C, 56.07; H, 3.86; N, 5.95 Infrared spectrum (KBr,cm$^{-1}$):

| 1350, 1520 | (NO$_2$) |
| 1700 | (CO) |
| 2115 | (C≡C) |
| 3000 | (OH) |
| 3275 | (C≡CH) |

Reference 1

2-(3-nitro-4-methoxyphenyl)propionic acid 5.23g of 2-(4-methoxyphenyl)propionic acid was added gradually under cooling in a mixture of 27.5g of nitric acid and 19.9g of sulfuric acid. After the mixture was stirred at −10° C to −5° C for 6 hours, the mixture was poured into ice-water. The thus obtained oily substance was extracted with ethyl acetate. The extract was dried over magnesium sulfate and distilled off. The residue was purified by means of silica gel chromatography to give the object compound having m.p. 89° – 90° C in a yield of 5.0g (76%).

Infrared spectrum (Nacl, cm$^{-1}$):

| 1350, 1530 | (NO$_2$) |
| 1710 | (CO) |
| 3000 | (OH) |

Elementary analysis for $C_{10}H_{11}NO_5$ (%) Calculated: C, 53.33; H, 4.92; N, 6.22 Found : C, 53.23; H, 4.72; N, 6.12.

Reference 2

2-(3-nitro-4-hydroxyphenyl)propionic acid

In a mixture of 125g of hydrobromic acid and 25ml of acetic acid 5g of 2-(3-nitro-4-methoxyphenyl)propionic acid was added and refluxed overnight. The solvent was concentrated to give crystals, which were filtered out and dried. Yield, 3.2g (68%). The crystals were recrystallized from water to give the object compound having m.p. 127 - 128° C.

Infrared spectrum (KBr, cm$^{-1}$):

| 1305, 1540 | (NO$_2$) |
| 1700 | (CO) |
| 3000 | (OH) |

Elementary analysis for $C_9H_9NO_5$ (%) Calculated: C, 51.19; H, 4.30; N, 6.63 Found : C, 51.21; H, 4.03; N, 6.52.

Reference 3

Ethyl 2-(3-nitro-4-hydroxyphenyl)propionic acid

In a mixture of 50ml of ethanol and 10 drops of sulfuric acid 3.2g of 2-(3-nitro-4-hydroxyphenyl)propionic acid was heated on a water bath for 5 hours. The solvent was concentrated and the residue was dissolved in ethyl acetate. After washing with water and drying, the solution was concentrated to give an oily substance in a yield of 3.2g (88%).

Infrared spectrum (KBr, cm$^{-1}$):

| 1310, 1540 | (NO$_2$) |
| 1730 | (CO) |
| 3300 | (OH) |

Elementary analysis for $C_{11}H_{13}NO_3$ Calculated: C, 55.23; H, 5.48; N, 5.86 Found : C, 55.13; H, 5.52; N, 5.76.

EXAMPLE 5

Methyl 2-(3-nitro-4-allyoxyphenyl)propionate

A mixture of 2.25g of methyl 2-(3-nitro-4-hydroxyphenyl)propionate, 1.45g of allylbromide and 1.65g of potassium carbonate in 40ml of acetone was refluxed for 4 hours. After cooling, the solvent was distilled under reduced pressure. The residue was dissolved in ethyl acetate and washed with water. After the solution was dried over Magnesium sulfate, the solvent was distilled off. The thus obtained oily substance was purified by means of silica gel chromatography to give the object compound having m.p. in a yield of 2.32g (92%).

Elementary analysis for $C_{13}H_{15}NO_5$ (%) Calculated: C, 58.86; H, 5.70; N, 5.28 Found : C, 58.56; H, 5.60; N, 5.38 Infrared spectrum (Nacl, $cm^{-1}$):

| 1350, 1530 | $(NO_2)$ |
|---|---|
| 1730 | (CO) |

EXAMPLE 6

Ethyl 2-(3-nitro-4-allyloxyphenyl)propionate

A mixture of 2.39g of ethyl 2-(3-nitro-4-hydroxyphenyl)propionate, 1.45g of allylbromide and 1.65g of potassium carbonate in 20ml of acetone was refluxed for 4 hours. After cooling, the solvent was distilled under reduced pressure. The residue was dissolved in ethyl acetate and washed with water. After the solution was dried over magnesium sulfate, the solvent was distilled off. The thus obtained oily substance was purified by means of silica gel chromatography, to give the object compound in a yield of 2.51g (90%).

Elementary analysis for $C_{14}H_{17}NO_5$ (%) Calculated: C, 60.20; H, 6.14; N, 5.02 Found : C, 60.25; H, 6.34; N, 5.19 Infrared spectrum (Nacl, $cm^{-1}$):

| 1350, 1520 | $(NO_2)$ |
|---|---|
| 1730 | (CO) |

EXAMPLE 7

2-(3-nitro-4-allyloxyphenyl)propionic acid

In a mixture of 0.45g of sodium hydroxide, 4ml of water and 10ml of methanol 1g of ethyl 2-(3-nitro-4-allyloxyphenyl)propionate was heated on a water bath for 30 minutes. After cooling, the mixture was neutralized with 10% hydrochloric acid and the thus obtained oily substance was extracted with ethyl acetate. After the extract was dried over magnesium sulfate, the solvent was distilled off to give crystals, which were recrystallized from ether-n-hexane to give the object compound having m.p. 64.5° – 65.5° C in a yield of 0.82g (91%).

Elementary analysis for $C_{12}H_{13}NO_5$ (%) Calculated: C, 57.37; H, 5.22; N, 5.58 Found : C, 57.27; H, 5.32; N, 5.60 Infrared spectrum (KBr, $cm^{-1}$):

| 1350, 1530 | $(NO_2)$ |
|---|---|
| 1710 | (CO) |
| 3000 | (OH) |

EXAMPLE 8

Methyl 3-nitro-4-methallyloxyphenylacetate

A mixture of 2.11g of methyl 3-nitro-4-hydroxyphenylacetate, 2.27g of methallyl p-toluenesulfonate was refluxed for one hour in 60ml of methanol containing natrium methoxide (natrium 0.25g). The reaction mixture was concentrated under reduced pressure and ethyl acetate and water were added to the residue. The ethyl acetate layer was isolated, and washed with water. After the extract was dried over magnesium sulfate, the solvent was distilled off and the residue was recrystallied from methanol to give the object compound having m.p. 30°- 31.5° C in a yield of 1.98g (74%).

Elementary analysis for $C_{13}H_{15}NO_5$ (%) Calculated: C, 58.86; H, 5.70; N, 5.28 Found : C, 58.84; H, 5.68; N, 5.31 Infrared spectrum (KBr, $cm^{-1}$):

| 1350, 1535 | $(NO_2)$ |
|---|---|
| 1735 | (CO) |

EXAMPLE 9

3-nitro-4-methallyloxyphenylacetic acid

In a mixture of 0.35g of sodium hydroxide, 3.5ml of water and 2ml of methanol 0.75g of methyl 3-nitro-4-methallyloxyphenylacetate was heated in a water bath for 30 minutes. After cooling, the reaction mixture was filtered and neutralized with 10% hydrochloric acid to give crystals, which were filtered out and recrystallized from methanol in a yield of 0.52g (73%). m.p. 119° – 120.5° C Elementary analysis for $C_{12}H_{13}NO_5$ (%) Calculated: C, 57.37; H, 5.22; N, 5.58 Found: C, 57.35; H, 5.37; N, 5.64 Infrared spectrum (KBr, $cm^{-1}$):

| 1350, 1530 | $(NO_2)$ |
|---|---|
| 1710 | (CO) |
| 3000 | (OH) |

Reference 4

Methyl 2-(4-hydroxyphenyl)propionate

In a mixture of 12ml of hydroiodic acid, 90ml of acetic acid and 1g of phosphorus 10g of 2-(4-methoxyphenyl)propionic acid was refluxed for 3 hours and the reaction mixture was concentrated. 20ml of methanol and 2ml of sulfuric acid were added to the residue and the mixture was refluxed for one hour. After the methanol was concentrated, the water was added to the residue and extracted with ether. The extract was washed over magnesium sulfate and the ether was distilled off. The residue was distilled under reduced pressure to give the object compound having b.p. 150° – 153° C/6mm Hg in a yield of 6.7g (67%)

Reference 5

2-(3-nitro-4-hydroxyphenyl)propionic acid

In a mixture of 8ml of nitric acid and 15ml of acetic acid 1g of 2-(4-hydroxyphenyl)propionic acid was added and stirred at −10° to −20° C for 4 hours. The reaction mixture was poured into ice water and extracted with chloroform. The extract was washed with a sodium hydrogen carbonate solution and water and then dried over magnesium sulfate. The chloroform solution was concentrated to give crystals, which were recrystallized from water. Yield, 700 mg (58%).

The physical data and m.p. coincided with those of the compound as described above.

Reference 6

Methyl 2-(3-nitro-4-hydroxyphenyl)propionate

In a mixture of 18ml of nitric acid and 30ml of acetic acid 2.76g of methyl 2-(4-hydroxyphenyl)propionate was stirred at −10° to −20° C for 4 hours. The reaction mixture was poured into ice water and extracted with chloroform. The extract was washed with a sodium hydrogen carbonate solution and water and dried over magnesium sulfate. The chloroform was distilled off to give the desired compound in a yield of 2.35g (69%). The physical data of this compound coincided with those of the compound as described above.

EXAMPLE 10

3-nitro-4-allyoxyphenylacetic acid a 3-nitro-4-hydroxyphenylacetamide

In 10ml of acetone 0.4g of 3-nitro-4-hydroxybenzylcyanide was dissolved and 0.9ml of 10% hydrogen peroxide was added thereto. This solution was stirred overnight at room temperature after adding a solution of 0.2g of sodium hydroxide in 0.7ml to this solution under cooling. Then, the acetone was distilled under reduced pessure and the residue was neutralized with 10% hydrochloric acid and extracted with ethyl acetate. After the extract was dried over magnesium sulfate, the ethyl acetate was distilled to give the object crystals in a yield of 0.437g (99.3%), which were recrystallized from ethyl acetate to give the object compound having m.p. 160.5° − 161° C.

Infrared spectrum (KBr, cm$^{-1}$):

| 1530, 1330 | (NO$_2$) |
|---|---|
| 1650 | (CO) |
| 3200 | (OH) |
| 3380 | (NH$_2$) |

Elementary analysis for C$_8$H$_8$N$_2$O$_4$ (%) Calculated: C, 48.98; H, 4.11; N, 14.28 Found: C, 48.78; H, 4.01; N, 14.38.

b 3-nitro-4-allyoxyphenylacetamide

In 20ml of acetone a mixture of 0.39g of 3-nitro-4-hydroxyphenylacetamide, 0.29g of allyl-bromide and 0.33g of potassium carbonate was refluxed for 5 hours. After the acetone was concentrated, water was added to the residue and extracted with ethyl acetate. After the extract was dried over magnesium sulfate, the extract was distilled to give crystals, which were recrystalized from ethyl acetate to give the object compound having m.p. 122° − 122.5° C. Yield, 0.39g (84.8%).

Infrared spectrum (KBr, cm$^{-1}$):

| 1350, 1530 | (NO$_2$) |
|---|---|
| 1630 | (CO) |
| 3380 | (NH$_2$) |

Elementary analysis for C$_{11}$H$_{12}$N$_2$O$_4$ (%) Calculated: C, 55.93; H, 5.12; N, 11.86 Found: C, 55.47; H, 5.24; N, 11.81.

c 3-nitro-4-allyoxyphenylacetic acid

In a mixture of 0.1g of potassium hydroxide, 0.5ml of water and 3ml of ethanol 0.236g of 3-nitro-4-allyloxyphenylacetamide was refluxed for 8.5 hours. After the ethanol was distilled off, water was added and the mixture was washed with ethyl acetate. After neutralization, the water layer was extracted with ethyl acetate. After the extract was dried over magnesium sulfate, the ethyl acetate was distilled to give crystals, which were recrystallized from ether petrolium ether to give the compound having m.p. 93° − 94° C.

Yield, 0.21g (88.7%).

Elementary analysis for C$_{11}$H$_{11}$NO$_5$ (%) Calculated: C, 55.69; H, 4.67; N, 5.91 Found: C, 55.40; H, 4.69; N, 5.68 Infrared spectrum (KBr, cm$^{-1}$):

| 1340, 1520 | (NO$_2$) |
|---|---|
| 1690 | (CO) |
| 3000 | (OH) |

EXAMPLE 11

3-Nitro-4-allyoxyphenylacetic acid a 3-Nitro-4-allyoxybenzylcyanide

In 20ml of acetone a mixture of 0.72g of 3-nitro-4-hydroxybenzylcyanide, 0.58g of allyl-bromide and 10.66g of potassium carbonate was refluxed for 5 hours. After distillation of acetone, the residue was extracted with ethyl acetate. After the extract was dried over magnesium sulfate, the ethyl acetate was distilled off and the residue was recrystallized from benzene-hexane to give the compound having m.p. 54° − 56.6° C. Yield, 0.77g (87.5%).

Elementary analysis for C$_{11}$H$_{10}$N$_2$O$_3$ (%) Calculated: C, 60.54; H, 4.62; N, 12.84 Found: C, 60.44; H, 4.59; N, 12.74 Infrared spectrum (KBr, cm$^{-1}$):

| 1350, 1530 | (NO$_2$) |
|---|---|
| 2230 | (CN) | b 3-nitro-4-allyoxyphenylacetic acid

In a mixture of 0.2g of potassium hydroxide, 1ml of water and 5ml of ethanol 0.25g of 3-nitro-4-allyloxybenzylcyanide was reflux for 7.5 hours. After neutralization, the reaction mixture was extracted with ethyl acetate and after the extract was dried over magnesium sulfate, the extract was distilled off to give the compound, which was identical with the compound obtained by example 10 (c) at all points of elementary analysis and infrared spectrum. Yield, 0.155g (57.4%).

Reference 7

3-Nitro-hydroxybenzylcyanide

In 20ml of ethanol a mixture of 1.87g of 3-nitro-4-hydroxybenzylchloride, 1.3g of potassium cyanide and 1.5g of potassium iodide was refluxed for 6 hours. After cooling and addition of water, the reaction mixture was extracted with ether. After the extract was dried over magnesium sulfate, the solvent was distilled off to give crystals in a yield of 1.43g, which were recrystallized from benezene to give the compound having m.p. 121° – 123° C.

Infrared spectrum (KBr, cm$^{-1}$):

| | |
|---|---|
| 1530, 1330 | ($NO_2$) |
| 2240 | ($C\equiv N$) |
| 3230 | (OH) |

What is claimed is:

1. A compound having the following formula:

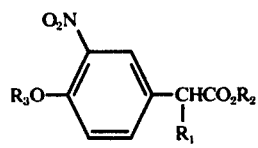

wherein $R_1$ represents a hydrogen atom or lower alkyl radical having 1-4 carbon atoms, $R_2$ represents an alkyl, phenyl, alkyl phenyl wherein the alkyl has from 1 to 4 carbon atoms, halogen-substituted phenyl wherein the halogen is chlorine or bromine, or alkoxy-substituted phenyl wherein the alkoxy is methoxy or ethoxy, and $R_3$ represents an alkenyl or alkynyl radical, both of which have 3–4 carbon atoms, and having the following formula:

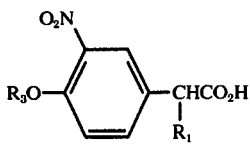

wherein $R_1$ and $R_3$ have the same meaning as above, or a pharmaceutically acceptable salt thereof.

2. A compound as claimed in claim 1 wherein the compound is selected from the group consisting of:
Methyl 3-nitro-4-allyloxyphenylacetate,
3-Nitro-4-allyloxyphenylacetic acid,
3-Nitro-4-propargyloxyphenylacetic acid,
Methyl 3-nitro-4-propargyloxyphenylacetate,
Methyl 2-(3-nitro-4-allyloxyphenyl)propionate,
Ethyl 2-(3-nitro-4-allyloxyphenyl)propionate,
2-(3-nitro-4-allyloxyphenyl)propionic acid,
Methyl 3-nitro-4-methallyloxyphenylacetate, and
3-Nitro-4-methallyloxyphenylacetic acid.

3. Methyl 3-nitro-4-allyloxyphenylacetate of claim 1.

4. 3-Nitro-4-allyloxyphenylacetic acid of claim 1.

5. 3-Nitro-4-propargyloxyphenylacetic acid of claim 1.

6. Methyl 3-nitro-4-propargyl-oxyphenylacetate of claim 1.

7. Methyl 2-(3-nitro-4-allyloxyphenyl)propionate of claim 1.

8. Ethyl 2-(3-nitro-4-alkyloxyphenyl)propionate of claim 1.

9. 2-(3-Nitro-4-allyloxyphenyl)propionic acid of claim 1.

* * * * *

UNITED STATES PATENT AND TRADEMARK OFFICE
CERTIFICATE OF CORRECTION

PATENT NO. : 4,016,193

DATED : April 5, 1977

INVENTOR(S) : TOSHIHIKO KOBAYASHI et al

It is certified that error appears in the above-identified patent and that said Letters Patent are hereby corrected as shown below:

Column 8, Table 1: delete the Table in entirety and replace with the following:

| | Name of compounds | dosage (mg/kg) orally | inhibiting rate (%) |
|---|---|---|---|
| Compounds of this invention | Methyl 3-nitro-4-allyl-oxyphenylacetate | 12.5<br>25 | 51.7<br>72.1 |
| | 3-Nitro-4-allyloxy-phenylacetic acid | 12.5<br>25<br>50 | 13.9<br>24.3<br>66.6 |
| | 3-Nitro-4-propargyloxy-phenylacetic acid | 50<br>100 | 28.8<br>40.3 |
| | Methyl 3-nitro-4-propargyl-oxyphenylacetate | 100 | 44.9 |
| | Methyl 2-(3-nitro-4-alloxyphenyl)propionate | 100 | 50.1 |
| | Ethyl 2-(3-nitro-4-allyloxyphenyl)propionate | 100 | 55.5 |
| | 2-(3-nitro-4-allyl-oxyphenyl)propionic acid | 100 | 40.1 |
| | 3-nitro-4-allyloxy-phenylacetamide | 100 | 37.7 |

Page 1 of 4

UNITED STATES PATENT AND TRADEMARK OFFICE
CERTIFICATE OF CORRECTION

PATENT NO. : 4,016,193
DATED : April 5, 1977
INVENTOR(S) : TOSHIHIKO KOBAYASHI et al It is certified that error appears in the above-identified patent and that said Letters Patent are hereby corrected as shown below:

(Table 1, continued)

| | | | |
|---|---|---|---|
| Known compounds | 3-chloro-4-allyloxy-phenylacetic acid | 25<br>50<br>100 | 47.0<br>51.8<br>62.0 |
| | Phenylbutazone | 12.5<br>25<br>50 | 14.1<br>49.1<br>59.4 |
| | Indomethacine | 1<br>3<br>9 | 39.8<br>46<br>60.4 |
| | Mepirizole | 25<br>50<br>100 | 19.5<br>51.8<br>52.7 |

---

UNITED STATES PATENT AND TRADEMARK OFFICE
CERTIFICATE OF CORRECTION

PATENT NO. : 4,016,193  Page 3 of 4
DATED : April 5, 1977
INVENTOR(S) : TOSHIHIKO KOBAYASHI et al It is certified that error appears in the above-identified patent and that said Letters Patent are hereby corrected as shown below:

Column 9, Table 2: delete the Table in entirety and replace with the following:

|  | Name of compounds | $ED_{50}$ (mg/kg) orally | activity ratio |
|---|---|---|---|
| Compounds of this invention | Methyl 3-nitro-4-allyl-oxyphenyl acetate | 31.0 | 1 |
|  | 3-nitro-4-allyloxyphenyl-acetic acid | 96.0 | 0.32 |
| Known compounds | 3-chloro-4-allyloxy-phenylacetic acid | 56.8 | 0.54 |
|  | Aminopyrine | 80.0 | 0.38 |
|  | Aspirin | 320.0 | 0.09 |
|  | Mepirizole | 117.0 | 0.26 |

Column 9, Table 3: in the last column:
before "above", "1,475", "1,700" and "1,022", insert --- ♂ ---;
before "3,000", "1,360", "1,630", and "971", insert --- ♀ ---.

UNITED STATES PATENT OFFICE
CERTIFICATE OF CORRECTION

Patent No. 4,016,193    Dated April 5, 1977

Inventor(s) Toshihiko Kobayashi et al.

It is certified that error appears in the above-identified patent and that said Letters Patent are hereby corrected as shown below:

Column 16, line 19: rewrite "ether petrolium" as -- ether-petrolium --.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks